United States Patent [19]

Schumacher et al.

[11] Patent Number: 5,399,345
[45] Date of Patent: Mar. 21, 1995

[54] MUTEINS OF THE GRANULOCYTE COLONY STIMULATING FACTOR

[75] Inventors: Gunter Schumacher, Bernried; Carola Dony, Starnberg, both of Germany

[73] Assignee: Boehringer Mannheim, GmbH, Mannheim, Germany

[21] Appl. No.: 960,982

[22] Filed: Oct. 14, 1992

Related U.S. Application Data

[63] Continuation-in-part of Ser. No. 696,794, May 8, 1991, abandoned.

[30] Foreign Application Priority Data

May 8, 1990 [DE] Germany .................. 40 14 750.9

[51] Int. Cl.$^6$ .................. A61K 31/00; C07K 13/00; C12P 21/00
[52] U.S. Cl. .................. 424/85.1; 435/69.5; 530/351; 930/145; 514/12
[58] Field of Search .................. 530/351; 930/145; 424/85.1; 435/69.5

[56] References Cited

U.S. PATENT DOCUMENTS 4,810,643 3/1989 Souza .................. 435/69.5

OTHER PUBLICATIONS

Okake et al., Blood, 75, 1990, pp. 1788–1793.
Gaertner et al., Bioconjugate Chem., 3(3), 1992, pp. 262–268, (abstract only).
Itoh et al., "Effects of Recombinant Human G–CSF on Primary Human Leukemic Cells", *Acta Haematologica Japonica*, pp. 988–995, (1989).

*Primary Examiner*—Garnette D. Draper
*Assistant Examiner*—Sally Teng
*Attorney, Agent, or Firm*—Nikaido, Marmelstein, Murray & Oram

[57] ABSTRACT

A granulocyte stimulating factor (G-CSF) or a G-CSF variant differs from natural G-CSF in that one or several amino acids of the sequence

```
50   51   52   53   54   55   56
Leu—Gly—His—Ser—Leu—Gly—Ile
``` at position 50 to 56 of the mature G-CSF with 174 amino acids or at position 53 to 59 of the mature G-CSF with 117 amino acids or/and at least one of the 4 His residues at position 43, 79, 156 or 170 of the mature G-CSF with 174 amino acids position 46, 82, 159 or 173 of the mature G-CSF with 177 amino acids are mutagenized. It is suitable for immunotherapy.

4 Claims, No Drawings

MUTEINS OF THE GRANULOCYTE COLONY STIMULATING FACTOR

CROSS REFERENCE TO RELATED APPLICATION

This is a continuation-in-part application of U.S. Ser. No. 07/696,794, filed May 8, 1991, now abandoned.

DESCRIPTION

The invention concerns muteins of the granulocyte stimulating factor G-CSF ill the sequence

```
     50   51   52   53   54   55   56
    Leu--Gly--His--Ser--Leu--Gly--Ile
``` at position 50 to 56 of the mature G-CSF with 174 amino acids or at position 53 to 59 of the mature G-CSF with 177 amino acids or/and at least one of the 4 His residues at positions 43, 79, 156 and 170 of the mature G-CSF with 174 amino acids or at positions 46, 82, 159 or 173 of the mature G-CSF with 177 amino acids.

Lymphokines are involved in the maturation of blood cells. They stimulate the maturation of bone marrow stem cells to fully differentiated cells. G-CSF is synthesized by activated monocytes, macrophages as well as by a series of other cell lines.

G-CSF was purified to homogeneity from cell culture supernatants of the human bladder carcinoma cell line 5637 (Welte et al., Proc. Natl. Acad. Sci 82 (1985), 1526). The sequence of the cDNA coding for native G-CSF is known from Souza et al., Science 232 (1986), 61. As a consequence of alternative splicing ill the second intron two naturally occurring forms of G-CSF exist with 204 or 207 amino acids of which the first 30 represent a signal peptide (Lymphokines, IRL Press, Oxford, Washington D.C., Editors D. Male and C. Rickwood). The mature protein has a molecular weight of ca.19.6 kD and has 5 cysteine residues which can form intermolecular or intramolecular disulphide bridges. Binding studies have shown that G-CSF binds to neutrophilic granulocytes. None or only slight binding is observed with erythroid, lymphoid eosinophilic cell lines as well as with macrophages. The G-CSF receptor consists of a single peptide chain with a molecular weight of 150 kD (Nicola, Immunol. Today 8 (1987), 134). The number of receptors per cell generally increases with the maturation of the cells and can amount to several hundred per cell. It is assumed that lymphokine receptors consist of an extracellular domain, which binds the ligands, a hydrophobic transmembrane region and an intracellular domain. Binding of lymphokines to their receptor can cause the synthesis of cyclic nucleotides, hydrolysis of phosphatidylinositol-4,5-biphosphate as well as the activation of protein kinase C and an increase in the intracellular calcium level. There is a great interest in how these processes effect the metabolism of the cell but at present they are hardly understood. A further result of the binding of a ligand to its receptor can be the migration of the receptor-ligand complex into the inside of the cell by a receptor-dependent endocytosis. This type of internalization apparently also occurs with lymphokines (e.g. G-CSF), however, the consequences for the metabolism of the cell are not yet understood.

Since G-CSF is able to substantially increase the population of neutrophilic granulocytes within a short period, considerable therapeutic fields of application arise for G-CSF. Thus, G-CSF could be used e.g. after chemotherapy in cancer, in which the cells of the immune system are destroyed. In addition G-CSF could be used in bone marrow transplantations, in severe burn wounds, in opportunistic infections caused by immune deficiency and in leukemia. For the different types of therapy it would be desirable to develop more active and also less active forms of G-CSF. The object of the present invention is therefore to develop G-CSF molecules with a wide spectrum of activity by the specific introduction of point mutations. In this process the changes in activity should be achieved by changes in the amino acid sequence which are as small as possible.

The object according to the present invention is achieved by a granulocyte stimulating factor (G-CSF) or a G-CSF variant, in which one or several amino acids of the sequence Leu-Gly-His-Ser-Leu-Gly-Ile at position 50 to 56 of the mature G-CSF with 174 amino acids or at position 53 to 59 of the mature G-CSF with 177 amino acids or/and at least one of the 4 His residues at position 43, 79, 156 or 170 of the mature G-CSF with 174 amino acids or at position 46, 82, 159 or 173 of the mature G-CSF with 177 amino acids are mutagenized.

Surprisingly the introduction of new amino acids yields G-CSF muteins which have a broad spectrum of activity. The determination of the activity can for example be carried out according to Biochem. J. 253 (1988) 213–218; Exp. Hematol. 17 (1989) 116–119; Proc. Natl. Acad. Sci. USA 83 (1986) 5010.

The term G-CSF or G-CSF variant according to the present invention includes all naturally occurring variants of G-CSF with or without a leader sequence as well as G-CSF proteins derived therefrom which are modified by recombinant DNA technology, in particular fusion proteins which contain further polypeptide sequences apart from the G-CSF moiety. In this sense a G-CSF mutein is particularly preferred with a N-terminal Met residue at position −1 which is suitable for expression in prokaryotic cells. Also preferred is a recombinant, methionine-free G-CSF variant which can be produced according to PCT/EP 91/00 192. The term "mutagenized" means that the respective amino acid is deleted or preferably substituted by another amino acid.

In this sense G-CSF muteins are preferred in which one of the 7 amino acids of the sequence Leu-Gly-His-Ser-Leu-Gly-Ile is substituted by another amino acid. However, more than one, ill particular two amino acids, can also be replaced.

A G-CSF mutein is particularly preferred ill which the Ser residue at position 53 of the mature G-CSF with 174 amino acids or at position 56 of the mature G-CSF with 177 amino acids is replaced by one of the other 19 amino acids, in particular by Thr.

Furthermore, it is preferred that the Leu residue at position 54 of the mature G-CSF with 174 amino acids or at position 57 of the mature G-CSF with 177 amino acids s substituted by one of the 19 other amino acids, in particular by Thr. By this means one obtains G-CSF muteins with a broad variation of G-CSF activity.

In addition G-CSF muteins are preferred in which one of the 4 His residues at position 43, 79, 156 or 170 of the mature G-CSF with 174 amino acids or at position 46, 82, 59 or 173 of the mature G-CSF with 177 amino acids is substituted by another amino acid, in particular Gln.

The invention also provides a recombinant DNA which codes for a G-CSF mutein according to the present invention. The invention also provides a recombinant vector which contains at least one copy of a recombinant DNA according to the present invention. In this connection a recombinant vector is preferred which is suitable for gene expression in prokaryotic cells. Vectors of this type are known to one skilled in the art.

In addition the invention provides a cell which is transformed with a recombinant DNA according to the present invention or/and a recombinant vector according to the present invention. This cell is preferably a prokaryotic cell, particularly preferably an E. coli cell.

The invention also provides a process for the production of a recombinant DNA according to the present invention in which a DNA sequence which codes for G-CSF or a G-CSF variant is site-specifically mutagenized. The usual molecular-biological methods for site-specific mutagenesis are known to one skilled in the art. The mutagenesis is preferably carried out by using synthetic oligonucleotides as mutagenesis primers on single-stranded DNA as the template. Common methods are for example described in Amersham No. 1523 "Oligonucleotide-directed in vitro mutagenesis system"; Methods in Enzymology (Academic Press, Inc. Vol. 154, Part E, 367–382 (1987); Analytical Biochemistry 179 (1989) 309–311.

In addition the invention provides a process for producing a G-CSF mutein according to the present invention in which a cell is transformed with a recombinant DNA according to the present invention or/and a recombinant vector according to the present invention, the transformed cell is cultured in a suitable medium and the protein is isolated from the cells or the medium. The methods usually used in molecular biology for the isolation of recombinant proteins from eukaryotic or prokaryotic cells are known to one skilled in the art and do not need to be elucidated in detail.

Finally the invention also provides a pharmaceutical preparation based on a G-CSF mutein according to the present invention as the active substance, if desired, together with the usual pharmaceutical carrier, filling and auxiliary substances. Such a pharmaceutical preparation is particularly suitable for the therapeutic fields of application mentioned above and even for further therapeutic proceedures in which the formation of neutrophilic granulocytes is to be stimulated.

The following examples are intended to elucidate the invention without however limiting its scope.

Example 1

Production of the vector mgl-G-CSF-Bg

The 554 bp long EcoRI/BamHI fragment from the vector pKK 177-3 G-CSF-Bg (DSM 5867) containing the Shine Dalgarno sequence, ATG codon and coding sequence for the G-CSF gene is cloned via a blunt-end ligation into the NcoI cleavage site of the vector pPZ 07-mgl lac (WO88/09373, FIG. 10). The ATG start codon of the lac Z gene, which is located in the protruding single strand after NcoI digestion, is digested beforehand by incubation with mung bean nuclease (Pharmacia). The resulting vector is denoted mgl-G-CSF-Bg.

Example 2

Mutagenesis of the amino acid Leu (X) in the sequence Gly-His-Ser-Leu-Gly-Ile The mutagenesis is carried out on the M13 template according to known techniques (Amersham No. 1523 "Oligonucleotide-directed in vitro mutagenesis system").

A 251 bp long G-CSF cDNA fragment is isolated via the cleavage site BstXI/AatII. The protruding single-strands are digested off by mung bean nuclease (Pharmacia) and the fragment is cloned into the vector M13mp19 which was cleaved with EcoRI/SmaI (EcoRI protruding single strand was filled in for blunt-end cloning). After preparing single-stranded DNA, the oligonucleotide is hybridized to the single-stranded DNA and an elongation in the 5'→3' direction beyond the oligonucleotide is carried out using Klenow polymerase, ligase and the four nucleotide triphosphates (GTP, CTP, TTP, ATP). The DNA which is now double-stranded is transformed in E. coli cells which carry a F' episome so that infection by filamentous M13 phages is possible (e.g. JM101, obtainable from Stratagene, LaJolla, Calif.). Individual plaques are picked out and the mutagenized M13 phages contained therein are used for the preparation of single-stranded DNA. A DNA sequencing is carried out according to known techniques (e.g. dideoxy method according to Sanger) and the exact substitution to form the desired mutation is checked in this way. After preparing double-stranded DNA the mutated AvaI fragment of G-CSF is isolated and cloned in the expression vector mgl-G-CSF-Bg (cleaved with AvaI).

In order to reconstitute the complete G-CSF gene the DNA is subsequently cleaved with HindIII, the protruding ends are filled in with Klenow polymerase and afterwards partially digested with AvaI so that the 5' AvaI site in the G-CSF gene (at ca 130 bp) is not cleaved. This DNA is ligated with the approximately 240 bp G-CSF fragment AvaI/BamHI (BamHI site is filled in with Klenow polymerase) from the starting vector mgl-G-CSF-Bg.

After transformation in E. coli JM83, the expression of G-CSF is carried out in the manner described in WO88/09373.

The cDNA used has a sequence which codes for a G-CSF with 175 amino acids (without a signal sequence, but with a Met residue at position −1) so that the preferred mutation is located at Leu at position 54 of the G-CSF amino acid sequence (in this the N-terminal Met residue is not counted).

The sequence of the cDNA (SEQ ID NO: 1) encoding G-CSF which codes for the amino acids 50 to 56 (with reference to the G-CSF with 174 amino acids) reads:

(X)
Leu—Gly—His—Ser—Leu—Gly—Ile
5'-CTC GGA CAC TCT CTG GGC ATC-3'

The corresponding complementary opposite strand (SEQ ID NO: 2) to be mutagenized reads:

5'-GAT GCC CAG AGA GTG TCC GAG-3'

The following 19 oligonucleotides corresponding to the opposite strand are used for site-directed mutagenesis:

| | | | | | | | | | |
|---|---|---|---|---|---|---|---|---|---|
| Wild-type: (SEQ ID NO: 2) | 5' → 3 | GAT | GCC | CAG | AGA | GTG | TCC | GAG | 3' |
| 1. (SEQ ID NO: 3) | 5' | GAT | GCC | Met CAT | AGA | GTG | TCC | GAG | 3' |
| 2. (SEQ ID NO: 4) | 5' | GAT | GCC | Phe GAA | AGA | GTG | TCC | GAG | 3' |
| 3. (SEQ ID NO: 5) | 5' | GAT | GCC | Gln CTG | AGA | GTG | TCC | GAG | 3' |
| 4. (SEQ ID NO: 6) | 5' | GAT | GCC | Glu CTC | AGA | GTG | TCC | GAG | 3' |
| 5. (SEQ ID NO: 7) | 5' | GAT | GCC | Asp GTC | AGA | GTG | TCC | GAG | 3' |
| 6. (SEQ ID NO: 8) | 5' | GAT | GCC | Cys GCA | AGA | GTG | TCC | GAG | 3' |
| 7. (SEQ ID NO: 9) | 5' | GAT | GCC | Ala GGC | AGA | GTG | TCC | GAG | 3' |
| 8. (SEQ ID NO: 10) | 5' | GAT | GCC | Gly AGG | AGA | GTG | TCC | GAG | 3' |
| 9. (SEQ ID NO: 11) | 5' | GAT | GCC | His GTG | AGA | GTG | TCC | GAG | 3' |
| 10. (SEQ ID NO: 12) | 5' | GAT | GCC | Ile GAT | AGA | GTG | TCC | GAG | 3' |
| 11. (SEQ ID NO: 13) | 5' | GAT | GCC | Lys CTT | AGA | GTG | TCC | GAG | 3' |
| 12. (SEQ ID NO: 13) | 5' | GAT | GCC | Tyr ATA | AGA | GTG | TCC | GAG | 3' |
| 13. (SEQ ID NO: 13) | 5' | GAT | GCC | Asn GTT | AGA | GTG | TCC | GAG | 3' |
| 14. (SEQ ID NO: 13) | 5' | GAT | GCC | Pro GGG | AGA | GTG | TCC | GAG | 3' |
| 15. (SEQ ID NO: 13) | 5' | GAT | GCC | Arg GCG | AGA | GTG | TCC | GAG | 3' |
| 16. (SEQ ID NO: 13) | 5' | GAT | GCC | Ser GGA | AGA | GTG | TCC | GAG | 3' |
| 17. (SEQ ID NO: 13) | 5' | GAT | GCC | Thr GGT | AGA | GTG | TCC | GAG | 3' |
| 18. (SEQ ID NO: 13) | 5' | GAT | GCC | Val GAC | AGA | GTG | TCC | GAG | 3' |
| 19. (SEQ ID NO: 13) | 5' | GAT | GCC | Trp CCA | AGA | GTG | TCC | GAG | 3' |

Example 3

Production of a G-CSF with modified activity

A G-CSF which is more enzymatically active compared to the wild-type can be produced by substituting serine at position 53 by a threonine at position 53 of a G-CSF with 174 amino acids (serine in the sequence Gly-His-Ser-Leu-Gly). The following double-stranded oligonucleotide (SEQ ID NO: 22 and SEQ ID NO: 23 ) was used for the mutagenesis:

```
                                          His Thr Leu Gly Ile
5' CCC GAG GAG CTG GTG CTG CTC GGA CAC ACC CTG GGC ATC CCC TGG GCT CCC CTG AGC 3'
3'          C CTC GAC CAC GAC GAG CCT GTG TGG GAC CCG TAG GGG ACC CGA GGG GAC 5'
```

For the cloning, the G-CSF cDNA fragment (ca 300 bp, EcoRI/EcoRV) from the vector pKK 177-3 G-CSF-Bg (DSM 5867) was ligated into the EcoRI/SmaI cleavage site of the vector pUC19 (Yannish-Perron et al., (1985), Gene 33, 103).

This DNA is cleaved with AvaI/SacI and directly ligated with the primer pair described above according to the usual techniques. The mutated BstIX/SacI fragment can now be isolated from this costruct and cloned into the vector pKK 177-3 G-CSF-Bg (DSM 5867) (cleaved with BstXI/SacI). The final construction of the expression clone is carried out ill analogy to Example 1. The determination of activity is carried out as described in Example 5.

Example 4

Alteration of the enzymatic properties of G-CSF by mutation of amino acids which are not located in the active center.

In analogy to known serine esterases it is assumed that the serine of the active centre interacts with histidine for the development of enzymatic activity. Four histidines which are present in the sequence of G-CSF (namely at positions 43, 79, 156 and 170, numbered from the 174 amino acid sequence without a signal peptide) are mutagenized. The histidine residue at position 52 (or at position 55 ill the 177 amino acid form) is left out of consideration in this mutagenesis. In this process His (CCA, CTA) is substituted by Gln (CAG). The sequence on the opposite strand corresponding to the codon coding for Gln is CTG.

A G-CSF fragment is subcloned in M13mp19 as described in Example 1.

The following oligonucleotides corresponding to the opposite strand are used for the mutagenesis:

(SEQ ID NO: 24)
1. 5' GCT CCT GGG CTG GCA CAG C 3'
histidine 43 to glutamine 43

(SEQ ID NO: 25)
2. 5' GAA AAG GCC GCT CTG GAG TTG GCT C 3'
histidine 79 to glutamine 79

(SEQ ID NO: 26)
3. 5' GCT CTG CAG CTG GCC TAG CAA CC 3'
histidine 156 to glutamine 156

(SEQ ID NO: 27)
4. 5' GGG CTG CGC AAG CTG GCG TAG AAC G 3'
histidine 170 to glutamine 170

The analytical procedure and the recloning in an expression vector is carried out in analogy to Example 1.

Example 5

Determination of the G-CSF activity

The activity of G-CSF is tested with the murine leukaemia line NSF60 which is completely dependent on G-CSF as described in Biochem. J. 253 (1988) 213–218, Exp. Hematol. 17 (1989) 116–119, Proc. Natl. Acad. Sci. USA 83 (1986) 5010. In order that the factor-dependency of the cells is preserved, the medium (RPMI medium, Boehringer Mannheim GmbH, Order No. 2099445 with 10% foetal calf serum) for the maintenance culture permanently contains 1000 U/ml G-CSF.

The proliferation of the NSF60 cells stimulated by G-CSF is measured directly in this test by the incorporation of $^3$H thymidine. The test is carried out as follows:

NSF60 cells which are in the exponential growth phase (cell density is maximally $1\times10^5$ cells/ml) are transferred to microtitre plates ($1\times10^4$ cells/well) and cultured with a decreasing G-CSF concentration. The maximum dose of G-CSF in well 1 corresponds to the concentration in the maintenance culture (1000 U/ml, specific activity $1\times10^8$ U/mg proteins). The dilution is carried out in steps of ten.

After about 24 hours incubation $^3$H thymidine (0.1 $\mu$Ci/well) is added. Afterwards the cells are incubated for a further 16 hours.

In order to evaluate the test the cells in the microtitre plates are frozen in order to lyse them. The cell lysate is aspirated on a glass fibre filter, rinsed, dried and measured in a scintillation counter. The incorporation of $^3$H thymidine is proportional to the G-CSF-induced proliferation of the NSF60 cells.

Example 6

Alteration in the activity of G-CSF by amino acid substitution in the active centre A G-CSF modified in amino acid position 54 can be produced by substitution of preferably one leucine at position 54 by a threonine at position 54 (Leu in the sequence Gly-His-Ser-Leu-Gly) in correspondence with the procedure described in Example 3 using a suitable double-stranded oligonucleotide which contains a nucleic acid triplet (e.g. ACC) coding for the amino acid Thr at the appropriate position. In this connection position 54 of the 174 amino acid form of G-CSF corresponds to position 57 of the 177 amino acid form.

The activity of a mutant having 174 amino acids with Thr at position 54 is reduced in the NSF60 cell test (see Example 5) in comparison to the wild-type G-CSF with 174 amino acids. Moreover, the activity of this G-CSF mutant is reduced in comparison to a G-CSF mutant with an amino acid substitution of a serine by a threonine at position 53 (described in Example 3).

TABLE 1

Designation of the Mutants (mutants prepared analogously to examples 2 and 3)

| Position | Designation | Mutation Type |
|---|---|---|
| | WT | Wild Type |
| 52 | HY | Histidine → Tyrosine |
| 52 | HS | Histidine → Serine |
| 52 | HR | Histidine → Arginine |
| 52 | HE | Histidine → Glutamine |
| 53 | ST | Serine → Threonine |
| 53 | SA | Serine → Alanine |
| 53 | SY | Serine → Tyrosine |
| 54 | LT | Leucine → Threonine |
| 54 | LH | Leucine → Histidine |
| 54 | LK | Leucine → Lysine |
| 52, 53 | HY:ST | Histidine → Tyrosine and Serine → Threonine |
| 52, 53, 54 | Del | Histidine, Serine, and Leucine → deleted |
| 52, 53, 54 | 3A | Histidine, Serine, and Leucine → Alanine |

TABLE 2

Activity of G-CSF Muteins (determined according to Example 5)

| Mutein | Activity |
|---|---|
| G-CSF not modified | 100 |
| HY | 75 |
| HS | 98 |
| HR | 88 |
| HE | 94 |
| ST | 93 |
| SA | 25 |
| SY | 33 |
| LT | 20 |
| LH | 22 |
| LK | 22 |
| Del | 2 |
| 3A | 24 |
| HY:ST | 42 |

We claim:

1. A granulocyte colony stimulating factor (G-CSF) mutein, wherein His at position 52 of a mature G-CSF with 174 amino acids is substituted with an amino acid selected from the group consisting of Ser, Arg and Glu.

2. A granulocyte colony stimulating factor (G-CSF) mutein, wherein Ser at position 53 of a mature G-CSF with 174 amino acids is substituted with Thr.

3. A pharmaceutical composition comprising at least one granulocyte colony stimulating factor (G-CSF) mutein, wherein His at position 52 of a mature G-CSF with 174 amino acids is substituted with an amino acid selected from the group consisting of Ser, Arg and Glu, in combination with a pharmaceutically acceptable carrier or filler.

4. A pharmaceutical composition comprising a granulocyte colony stimulating factor (G-CSF) mutein, wherein Ser at position 53 of a mature G-CSF with 174 amino acids is substituted with Thr, in combination with a pharmaceutically acceptable carrier or filler.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:1:

CTCGGACACT CTCTGGGCAT C         21

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: circular ( i i ) MOLECULE TYPE: DNA ( x i ) SEQUENCE DESCRIPTION: SEQ ID NO:2:

GATGCCCAGA GAGTGTCCGA G         21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GATGCCCATA GAGTGTCCGA G         21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GATGCCGAAA GAGTGTCCGA G         21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GATGCCCTGA GAGTGTCCGA G         21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GATGCCCTCA GAGTGTCCGA G      21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

GATGCCGTCA GAGTGTCCGA G      21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GATGCCGCAA GAGTGTCCGA G      21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GATGCCGGCA GAGTGTCCGA G      21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GATGCCAGGA GAGTGTCCGA G      21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:11:

GATGCCGTGA GAGTGTCCGA G                                                          21

( 2 ) INFORMATION FOR SEQ ID NO:12:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:12:

GATGCCGATA GAGTGTCCGA G                                                          21

( 2 ) INFORMATION FOR SEQ ID NO:13:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:13:

GATGCCCTTA GAGTGTCCGA G                                                          21

( 2 ) INFORMATION FOR SEQ ID NO:14:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:14:

GATGCCATAA GAGTGTCCGA G                                                          21

( 2 ) INFORMATION FOR SEQ ID NO:15:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:15:

GATGCCGTTA GAGTGTCCGA G                                                          21

( 2 ) INFORMATION FOR SEQ ID NO:16:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:16:

GATGCCGGGA GAGTGTCCGA G                                                          21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GATGCCGCGA GACTGTCCGA G        21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

GATGCCGGAA GAGTGTCCGA G        21

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

GATGCCGGTA GAGTGTCCGA G        21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

GATGCCGACA GAGTGTCCGA G        21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

GATGCCCCAA GAGTGTCCGA G        21

( 2 ) INFORMATION FOR SEQ ID NO:22:

( i ) SEQUENCE CHARACTERISTICS:
        ( A ) LENGTH: 57 base pairs
        ( B ) TYPE: nucleic acid ( C ) STRANDEDNESS: double
( D ) TOPOLOGY: linear ( i i ) MOLECULE TYPE: DNA ( x i ) SEQUENCE DESCRIPTION: SEQ ID NO:22:

CCCGAGGAGC TGGTGCTGCT CGGACACACC CTGGGCATCC CCTGGACTCC CCTGAGC    57

( 2 ) INFORMATION FOR SEQ ID NO:23:

( i ) SEQUENCE CHARACTERISTICS:
( A ) LENGTH: 49 base pairs
( B ) TYPE: nucleic acid
( C ) STRANDEDNESS: double
( D ) TOPOLOGY: linear ( i i ) MOLECULE TYPE: DNA ( x i ) SEQUENCE DESCRIPTION: SEQ ID NO:23:

CAGGGGAGCC CAGGGGATGC CCAGGGTGTG TCCGAGCAGC ACCAGCTCC    49

( 2 ) INFORMATION FOR SEQ ID NO:24:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:24:

GCTCCTGGGC TGGCACAGC    19

( 2 ) INFORMATION FOR SEQ ID NO:25:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:25:

GAAAAGGCCG CTCTGGAGTT GGCTC    25

( 2 ) INFORMATION FOR SEQ ID NO:26:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:26:

GCTCTGCAGC TGGCCTAGCA ACC    23

( 2 ) INFORMATION FOR SEQ ID NO:27:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:27:

GGGCTGCGCA AGCTGGCGTA GAACG 25